(12) United States Patent
Terekhov (10) Patent No.: US 11,872,388 B2
(45) Date of Patent: Jan. 16, 2024

(54) ELECTROSTIMULATION APPARATUS

(71) Applicant: VIKTOR S.R.L., Milan (IT)

(72) Inventor: Viktor Terekhov, Milan (IT)

(73) Assignee: VIKTOR S.R.L., Milan (IT)

( * ) Notice: Subject to any disclaimer, the term of this patent is extended or adjusted under 35 U.S.C. 154(b) by 817 days.

(21) Appl. No.: 16/478,428

(22) PCT Filed: Jan. 18, 2018

(86) PCT No.: PCT/IB2018/050299
§ 371 (c)(1),
(2) Date: Jul. 16, 2019

(87) PCT Pub. No.: WO2018/134753
PCT Pub. Date: Jul. 26, 2018

(65) Prior Publication Data
US 2021/0128904 A1 May 6, 2021

(30) Foreign Application Priority Data
Jan. 18, 2017 (IT) .................. 102017000005161

(51) Int. Cl.
*A61N 1/04* (2006.01)
*A61N 1/36* (2006.01)

(52) U.S. Cl.
CPC ......... *A61N 1/0452* (2013.01); *A61N 1/0456* (2013.01); *A61N 1/36003* (2013.01); *A61N 1/36034* (2017.08)

(58) Field of Classification Search
CPC .................. A61N 1/0452; A61N 1/36034
(Continued)

(56) References Cited

U.S. PATENT DOCUMENTS 4,785,813 A * 11/1988 Petrofsky ........... A61N 1/36003
607/48
5,277,197 A * 1/1994 Church .................. A61B 5/486
600/546
(Continued)

FOREIGN PATENT DOCUMENTS

CN 201431704 Y 3/2010
JP H04-224772 A 8/1992
(Continued)

OTHER PUBLICATIONS

Office Action for Japanese Patent Application No. 2019-559417 dated Jul. 6, 2022, 4 pages.
(Continued)

*Primary Examiner* — Carl H Layno
*Assistant Examiner* — Manolis Pahakis
(74) *Attorney, Agent, or Firm* — Merchant & Gould P.C.

(57) ABSTRACT

An electrostimulation method of at least one muscle group responsible for performing a complex movement includes associating to each of the muscles of the at least one muscle group an electrostimulation channel provided with at least one respective electrode. Each electrostimulation channel is suitable to transmit to the respective muscle bipolar electrical pulses in sequence. For all the electrostimulation channels, a same cycle time defining a repeatable period of stimulation is determined, in which, within the stimulation period, each channel performs its own stimulation sequence. Each stimulation period is sub-divided into two half-periods of equal duration. Each half-period is sub-divided into sub-intervals of the same duration. At least one of the sub-intervals is a stimulation sub-interval wherein a basic sequence of pulses including one or more pulse packets is performed, each pulse packet being given by a predetermined sequence of individual bipolar electric pulses.

16 Claims, 8 Drawing Sheets

(58) Field of Classification Search
USPC .......................................................... 607/48
See application file for complete search history.

(56) References Cited

U.S. PATENT DOCUMENTS

| | | | | |
|---|---|---|---|---|
| 5,433,737 | A * | 7/1995 | Aimone | A61N 1/36034 |
| | | | | 607/72 |
| 5,562,718 | A * | 10/1996 | Palermo | A61N 1/36021 |
| | | | | 607/46 |
| 7,369,896 | B2 * | 5/2008 | Gesotti | A61N 1/36003 |
| | | | | 607/45 |
| 8,660,651 | B2 * | 2/2014 | Castel | A61K 31/506 |
| | | | | 607/46 |
| 9,393,409 | B2 * | 7/2016 | Edgerton | A61N 1/0456 |
| 10,391,314 | B2 * | 8/2019 | Hoffer | A61B 5/4893 |
| 10,537,733 | B2 * | 1/2020 | Dixon | A61N 1/0484 |
| 10,625,074 | B2 * | 4/2020 | Rosenbluth | A61N 1/36178 |
| 11,484,709 | B2 * | 11/2022 | Verity | A61N 1/36003 |
| 2002/0183805 | A1 * | 12/2002 | Fang | A61N 1/37252 |
| | | | | 607/59 |
| 2002/0188331 | A1 * | 12/2002 | Fang | A61N 1/08 |
| | | | | 607/48 |
| 2004/0088025 | A1 * | 5/2004 | Gesotti | A61N 1/36003 |
| | | | | 607/49 |
| 2006/0122662 | A1 * | 6/2006 | Tehrani | A61B 5/395 |
| | | | | 607/42 |
| 2008/0167695 | A1 * | 7/2008 | Tehrani | A61N 1/3601 |
| | | | | 607/42 |
| 2008/0208287 | A1 * | 8/2008 | Palermo | A61N 1/36025 |
| | | | | 607/3 |
| 2008/0208288 | A1 * | 8/2008 | Gesotti | A61N 1/36003 |
| | | | | 607/48 |
| 2009/0187124 | A1 * | 7/2009 | Ludlow | A61H 23/00 |
| | | | | 601/47 |
| 2009/0326607 | A1 * | 12/2009 | Castel | A61N 1/36003 |
| | | | | 514/217 |
| 2011/0208266 | A1 * | 8/2011 | Minogue | A61B 5/296 |
| | | | | 607/49 |
| 2012/0158091 | A1 * | 6/2012 | Tehrani | A61N 1/3601 |
| | | | | 607/42 |
| 2014/0100638 | A1 | 4/2014 | Hou et al. | |
| 2014/0148873 | A1 * | 5/2014 | Kirn | A61N 1/20 |
| | | | | 607/49 |
| 2017/0028189 | A1 * | 2/2017 | Stanley | A61N 1/36031 |
| 2017/0157396 | A1 * | 6/2017 | Dixon | A61N 1/0452 |
| 2018/0093093 | A1 * | 4/2018 | Courtine | A61B 5/24 |
| 2018/0239430 | A1 * | 8/2018 | Tadi | G06F 3/015 |
| 2019/0247650 | A1 * | 8/2019 | Tran | A61N 1/3704 |
| 2019/0286234 | A1 * | 9/2019 | Condolo | G06Q 30/0242 |

FOREIGN PATENT DOCUMENTS

| | | |
|---|---|---|
| JP | 2006-020947 A | 1/2006 |
| JP | 2006-503658 A | 2/2006 |
| JP | 2011-110117 A | 6/2011 |
| RU | 2236264 C1 | 9/2004 |
| WO | 2006/045397 A1 | 5/2006 |
| WO | 2014/113813 A1 | 7/2014 |
| WO | 2016/013067 A1 | 1/2016 |
| WO | 2016/125312 A1 | 8/2016 |

OTHER PUBLICATIONS

International Search Report and Written Opinion of the International Searching Authority for International Patent Application No. PCT/IB2018/050299 dated Apr. 13, 2018, 12 pages.

Office Action for Japanese Patent Application No. 2019-559417 dated Aug. 24, 2021, 19 pages.

Russian Office Action for Russian Patent Application No. 2019125948/14(050871) dated Mar. 9, 2021, 2 pages.

* cited by examiner

ELECTROSTIMULATION APPARATUS

This application is a National Stage Application of PCT/IB2018/050299, filed 18 Jan. 2018, which claims benefit of Serial No. 102017000005161, filed 18 Jan. 2017 in Italy and which applications are incorporated herein by reference. To the extent appropriate, a claim of priority is made to each of the above-disclosed applications.

BACKGROUND OF THE INVENTION

The present invention relates to an electrostimulation method and apparatus of at least one muscle group responsible for carrying out a complex movement.

The proposed electrostimulation method and apparatus are aimed at treating problems related to the neuromuscular system, maintaining health in older people and electrophysiological training aimed at high-level athletic training.

In particular, the electrostimulation method and apparatus are used for:
- the treatment of neuromuscular diseases, spinal cord injuries and the peripheral and central nervous system in the phase of recovery from the loss of functions, including post-stroke;
- the treatment of all postoperative corrective orthopedic variants;
- functional correction for problems related to the motor system and old age;
- specialized high-level sports training, to train for speed and endurance;
- the prevention of neuromuscular traumas through specific training;
- functional monitoring during the workout.

The human body, and more specifically the neuro-muscular system, are very complex and articulated, but both function and are subject to the law of electrical transmission. In effect, nerve impulses travel and use the difference in electrical potential as the principal vehicle of communication.

When the nervous system, brain or spinal cord, is traumatized, either mechanically as a result of an accident or due to a stroke, to protect the damaged local structures, protective mechanisms of the spinal shock type begin to work automatically, tending to decrease the area of damage, but at the same time isolating the structures affected from every central control.

By following the natural principle that every organism tends toward less energy consumption, the damaged part is, so to speak, disconnected, thus depriving the person of control of the organs and the parts of the body normally controlled voluntarily by the person before the accident.

Cases wherein a spontaneous recovery manifests itself in a powerful way are rare; the situations are much more numerous that after trauma the situation does not change, remaining, in the best of cases, stable.

This lack of improvement is obviously partly due to the severity of the trauma and partly due to the inadequacy and the lack of effectiveness of the rehabilitative therapies currently implemented.

With specific regard to sports training, it is well known that modern sport, focused on achieving maximum results, presents a demand for athletic training at an increasingly high level. Athletes must devote at least 6-8 hours a day to intensive training, including at least 2 hours to improving technique and strength. Such a workout requires the athlete to exert all his/her mental and physical potential. Certainly not many athletes are able to fulfill such demands, and most of those who want to dedicate themselves to professional sport do not achieve the desired results because their athletic training does not meet the necessary requirements.

In most cases, the main parameters for evaluating sports performance are: strength, speed, stamina and repetition reliability of the athletic movement.

The qualities listed above are developed, for the various sports, during the athlete's training.

Such preparation is usually based on exercises repeated over time, performed consistently by different muscle groups, through multidisciplinary approaches.

The monotony of this type of training aimed at increasing strength is mainly characterized by the use of weightlifting equipment. However, this approach quickly causes fatigue, slows recovery and reduces the motivation necessary to maintain the athlete's competitive spirit.

In effect, functional electrical stimulation tools known as FES (functional electrical stimulation) are already known and used. However, their use is based on a substantially passive application of electrostimulation, which does not allow an action to be targeted on the peripheral nervous system.

According to the Applicant, however, it is necessary to provide an electrical stimulation recognizable by the nervous system as similar to the signal normally used by our bodies to produce movement.

In particular, passive electrostimulation, i.e. without movement, is not physiological, as it causes an information mismatch between the sensory system that controls muscle contraction.

During such passive electrostimulation, discordances are created between the information provided by the muscle receptors, and the information provided by proprioceptive joint sensors.

Moreover, due to inadequate electrical stimuli that do not take into account the parameters of the operation of the neuromuscular system, the biochemical reserves of acetylcholine are exhausted and the activation processes of the muscular fibers at the level of the end plate are violated.

SUMMARY OF THE INVENTION

The object of the present invention is to propose an electrostimulation method and apparatus capable of overcoming the above-mentioned limits of electrostimulation methods according to the state of the art, and in particular capable of generating electrical stimulation signals recognizable by the nervous system as similar to the signals normally used by our body to produce movement.

BRIEF DESCRIPTION OF THE DRAWINGS

The features and advantages of the electrostimulation method and apparatus according to the invention will, however, become evident from the description hereinafter of their preferred embodiments, provided by way of indicative and non-limiting examples, with reference to the accompanying figures, wherein.

DETAILED DESCRIPTION OF THE PREFERRED EMBODIMENTS

The basis of the present invention is the assumption that, with the repetition of movements, one reaches the optimization of the serial control mechanisms up to the (automated) segmental level. This movement control system allows maximum efficiency with minimum energy costs to tackle motor tasks with maximum speed and precision.

In a preferred embodiment, the movement program carried out using the electrostimulation method according to the invention provides synchronized electrostimulation of the muscles which meanwhile carry out the programmed cyclical movement. The programs are created on the polymyographic design of the movement, where each muscle is activated at a precise moment.

In particular, as a basis for creating electrostimulation programs that implement the method according to the invention, the biomechanical and polymyographic characteristics of healthy athletes with high athletic ability in performing particular exercises have been considered. The myographic recording of each exercise was performed using modern, 16-channel myographic systems with subsequent comprehensive analysis processing of the recorded data.

Therefore, all the electrostimulation programs created for the synchronized movement of the muscle groups necessary to perform a complex movement correspond to the physiological and biomechanical models of the same exercises.

Advantageously, the proposed electrostimulation method allows one to reproduce, through specific stimulation programs, the most important cyclic movements known, such as walking, running, jumping, bending, etc.

The movements may be performed at any rhythm, for example with a frequency of 0.2 to 10 seconds.

The proposed method allows electrostimulation to be carried out at the moment of the contraction specific to the muscle performing the programmed function. In this way the electrostimulation method may be considered "physiological", i.e. recognizable by the nervous system as similar to the signals normally used by our bodies to produce movement.

During the workout, not only the contraction of the muscle increases; at the same time, the related sensory system is activated. This is of great importance, since in the case of coordination discrepancy between the electrical exposure and neural programming of the motor neuron, the normal function of the motor neuron system could be interrupted, including the afferent information up to the cerebral cortex. In other words, the interneuronal connections created may also be broken by learning a new movement. This negative case is typical of the already existing electrostimulators that do not respect basic physiological rules.

In this regard, it should be noted that in the human brain memory, there are no stereotypes of movements, but rather the control algorithms of movements are adapted in real time to obtain the desired result with a rational use of the hierarchically subordinated neuro-muscular system.

The invention is based on the concept that the cyclic repetition of the movement optimizes and automates the movement control mechanisms at the segmental level. This in turn allows maximum efficiency and minimum energy consumption to resolve motor tasks with maximum speed and precision.

Each muscle group in the body is innervated and the motor neurons responsible for contraction are found in the spinal cord. The right half of the body is innervated by the corresponding motor neurons, as is the left; the sensory system stimulates the work of the related muscle groups, transmits the information in real time according to a subordination (hierarchy) in relation to the analysis carried out by the brain at the cortical level and by the spinal cord at the segmental and executive level responsible for muscle contraction.

In other words, the proposed electrostimulation method provides that the electrostimulation is carried out during the movement itself, rather than generating a movement.

By combining this type of electrostimulation with a complete range of exercises and physical movements repeated cyclically, one obtains the right mix to provide the nervous system with the appropriate stimuli to promote a recovery of function.

Especially in the case of stimulating the muscles of an athlete for the improvement of his/her performance, considering that an athlete, during the exercise of a given program, may not be able to match or continue to match his/her own rhythm or muscular activity at the rhythm of electrostimulation of the electrostimulation program, according to an aspect of the invention, the possibility is provided to modify automatically, i.e. without interrupting the stimulation exercise, the electrical stimulation rhythm in such a way as to follow that of the subject undergoing the stimulation treatment.

For this purpose, a sensorial tracking system is provided that automatically adjusts and synchronizes the electrostimulation cycle with the real muscle contraction modes.

The use of such an adaptive mode of functional electrical stimulation is particularly advantageous, not only during prolonged training of the neuromuscular system, but also in rehabilitation, since the resonance coupling helps to recreate the synaptic connections between interneurons and motor neurons, creating the conditions for restoring lost functions.

According to the current state of knowledge, five construction levels of movement may be identified in humans:

A—tone and posture level;
B—synergy level (coordinated muscle contraction);
C—sensory level;
D—mental logic level (semantic circuit);
E—symbolic coordination of cortical levels (writing, language, etc.).

Such levels, and their sensory correction, i.e., the ability to orientate oneself in space through the sensory inputs coming from sight, hearing, touch and proprioceptive sensation, are called "basic".

The higher level of motor control and its essential regulation is called "higher level". The higher level of regulation evaluates the result of the movement by comparing it with the planned one and makes some modifications based on the logical models of previous experiences, providing also the real capacity of the lower level up to the segmental level in the availability of which is found the anatomically organized system of sensory control of the movement.

Each level has a specific set of tools for the necessary corrections to the preset functions.

More precisely, each of the aforementioned levels has its own anatomically organized structure that performs a specific function for realizing the intended objective and also for automating the survival of the organism.

Each level of regulation corresponds to an anatomically organized structure, which allows a wide range of programmed functions to be performed and also, as needed, guarantees access to the coupled nerve structures.

Each of these levels contributes to the specific anatomical formation in the central nervous system, also through its sensorimotor correction tools.

The instruments specific to sensorimotor self-correction are anatomically present above all at levels A, B, C and perform their functions according to the principle of biofeedback at the interneuron level and by virtue of the synaptic activation mechanism and the inhibition of the specialized motor neurons in reciprocal regime.

The information concerning the correction carried out at a given level arrives through the sections belonging to the higher levels where it is processed and redirected towards the lower levels in the form of a new motor command.

The diversity of human motor activity is ensured by the management system, which connects specialized anatomical entities with the sensory system.

The motor regulating system of the human body was created in the process of evolutionary adaptation as a loop, essential in the composition of the human central nervous system according to the principle of multilevel hierarchical control, where each level is determined by its functional task, with a monitoring of the progress active on the local level and on the higher level.

The proposed electrostimulation method is designed to provide functional electrostimulation of the human locomotor system in accordance with the functioning of the anatomo-physiological laws of such locomotor system.

The proposed electrostimulation apparatus allows one to use electric pulses which are adjustable in power, duration, frequency, polarity and programmed repetition, so as to act on the neuro-muscular system during movement, or in isometric or isotonic mode both in exercise and without movement.

The proposed electrostimulation apparatus is equipped with a wide set of parameters of electrical pulses physiologically suitable for the correct functioning of the human neuromuscular system, with the possibility of storing the stimulation parameters for each program and for each patient.

From this derives the possibility to accumulate data related to the various training sessions and therefore to create a specific database for each pathology and each specialized training, allowing the workout method to be standardized for future sessions.

With these movement diagrams, it is possible to create a software library of functional electrostimulation programs, for example on 16 independent channels, which also reflect the rehabilitation statistics of the different cases.

The library of programs allows the coherent functional electrical stimulation of the main muscle groups, taking into account the anatomical-physiological laws of their simultaneous work on the electrostimulation channels used.

The electrostimulation programs are based on a wide range of cyclical movements, including movements applicable to fitness and weightlifting machines; they are developed based on polymyographical, goniometric and dynamometric examinations performed on high-level athletes, healthy children, adolescents and the elderly.

These programs form rules of models or protocols that allow one to attempt the rehabilitation of a wide range of diseases of the nervous system in all cases where one wishes to restore motor functions, as well as to provide athletes with a specialization in terms of speed, strength and power, and also to coach persons undergoing specialty training (astronauts, special forces, etc.).

The various programs are selected with respect to the specific pathology and the existing contraindications.

All the programs have been prepared taking into consideration the stimulation of the physiological models of joint movement of the lower and upper limbs.

In particular, the proposed electrostimulation method generates an impact on the upper and lower extremities according to physiological models of the movement thereof and is extremely important also in the neurological rehabilitation of pathological synergies (stroke).

A method of electrostimulation of at least one muscle group responsible for carrying out a complex movement according to a general embodiment of the invention will be described hereinafter.

The method provides for stimulating each muscle of each muscle group, associating to such muscle a respective electrostimulation channel of an electrostimulation apparatus which will be described further on.

Each electrostimulation channel is suitable to transmit to the respective muscle, by means of an electrode, or preferably a pair of electrodes, bipolar (and, with certain programs, monopolar) electric pulses in sequence.

In one embodiment, each channel is connected, by means of a cable, to two electrodes, for example, made of conductive rubber. An adhesive conductive gel may be applied to the surface of each electrode, providing reliable contact with the skin. Each pair of electrodes is placed over a muscle group to make the stimulation of the individual channel operative.

Each channel, with the exception of special cases, is always used on the same muscle group. Furthermore, the channels located symmetrically on each half of the body have their functional antagonist active which causes the contraction of the muscle in phase opposition with respect to the cyclic movement.

For example, in the case of 16 channels, 8 are the channels dedicated to the flexor muscle groups and the remaining 8 channels are dedicated to the extensor muscle groups. Consequently, during the cyclical movement, no more than 8 channels work simultaneously per functional group in turn, performing the complete cycle of the movement specified by the program.

Movement programs (or exercises) are linked to the myographic reference of the main muscle groups that allow human movement. The same is also true of specialized sports movements.

In particular, the electrostimulation of the muscle groups derives from the movement diagrams identified through the myographic devices.

This approach guarantees the myographic regularity of the muscles when performing the exercises, the same regularity that forms the basis of the movement programs.

The movement programs thus obtained are collected in the catalog of electrostimulation programs in the memory of the functional electrostimulation apparatus of the neuromuscular system.

The various channels work according to the specified program, and the moment of beginning stimulation, for each channel, causes the muscle under the electrode to contract.

In a healthy person, performing the movement according to the program selected in the specified rhythm (whereby the effective muscle contraction corresponds to the duration of the electrical power stimulus), leads to increasing the number of motor neurons recruited for the activation of the various motor units and to increasing consequently also the activated percentage of the same.

All reciprocal cyclical movements also have their own specifics of inclusion of the muscles of each half of the body. This also depends on the performance of the exercises, and therefore, to reconstruct the various movements, the characteristics of the contraction model of the muscle groups have been chosen using the polymyographic parameters of the main muscle groups involved in human movement.

Figure 1:
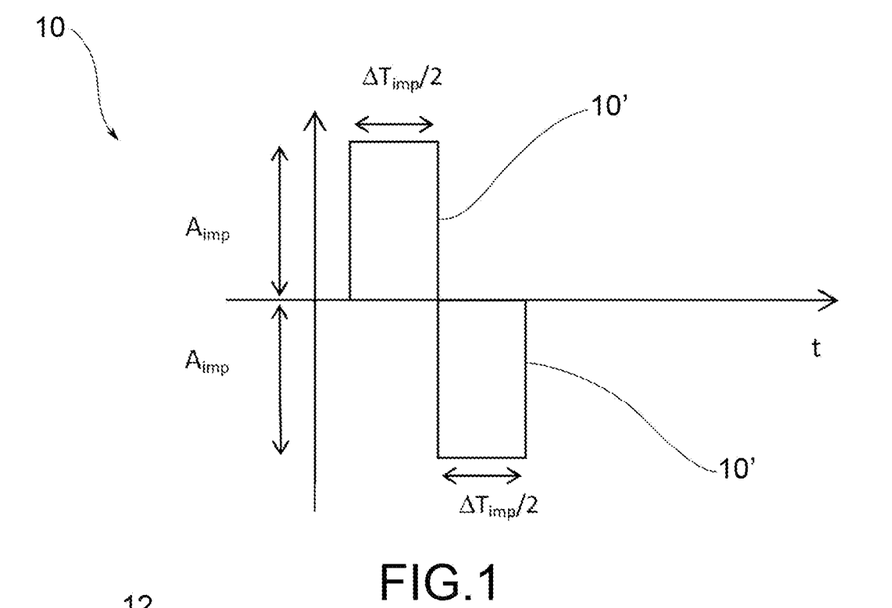
FIG. 1 shows an example of a bipolar pulse used for electrostimulation.

In an embodiment illustrated in FIG. 1, each bipolar electric pulse 10 is symmetrical and squared. Therefore, each bipolar pulse 10 consists of a square wave having a pulse period ΔTimp divided into two half-periods 10' of equal duration, one of positive amplitude and the other of negative amplitude.

Furthermore, according to the type of treatment to be performed on a given muscle, the first half-period may be positive and the second negative, or vice versa.

Therefore, the electrostimulation apparatus according to the invention allows the shape of the electrical signal to be selected, accentuating selectively the action on the ascending nerves (afferent, sensory) or on the motor nerves (efferent), thus offering further opportunities for specialized sports training, as well as for the treatment of any motor dysfunction.

More specifically, when a program with selection of afferent electrostimulation is desired, bipolar electric pulses are generated wherein the first half-period has a negative amplitude. In this way, the propagation of the excitation waves is toward the brain.

When a program with selection of efferent electrostimulation is desired, bipolar electric pulses are generated wherein the first half-period has a positive amplitude. In this way, the excitation wave generated by the first stimulus will be directed in the descending (efferent) direction to the muscles.

For all the electrostimulation channels "C", a same cycle time ΔTseq is established (FIG. 3), which defines a repeatable stimulation period "P". Within each stimulation period P, each channel C performs its own stimulation sequence. Therefore, an electrostimulation treatment is given by a repetition, for a pre-established workout time, of N stimulation periods, and therefore of N equal stimulation sequences.

Figure 3:
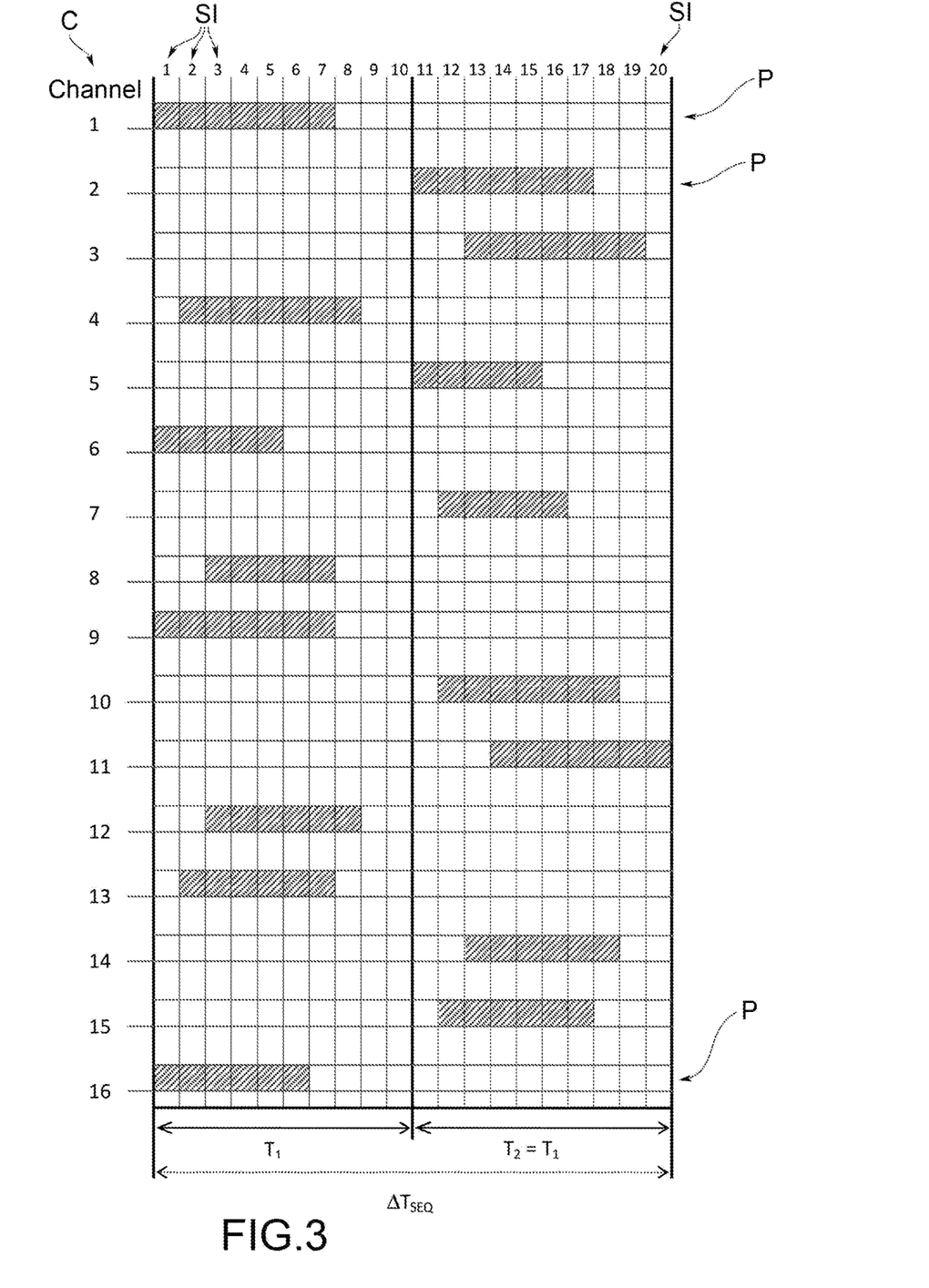
FIG. 3 shows, for a cycle of an electrostimulation program, the pulse packet sequences of the sixteen electrostimulation channels used.

Each stimulation period P is divided into two half-periods T1, T2 of equal duration.

Moreover, each half-period is divided into a plurality of sub-intervals "SI" of equal duration.

At least one of such sub-intervals SI is a stimulation sub-interval wherein a base sequence of pulses comprising one or more pulse packets 12 is carried out.

In turn, each pulse packet 12 is given by a predetermined sequence of individual bipolar electric pulses 10.

Figure 2:
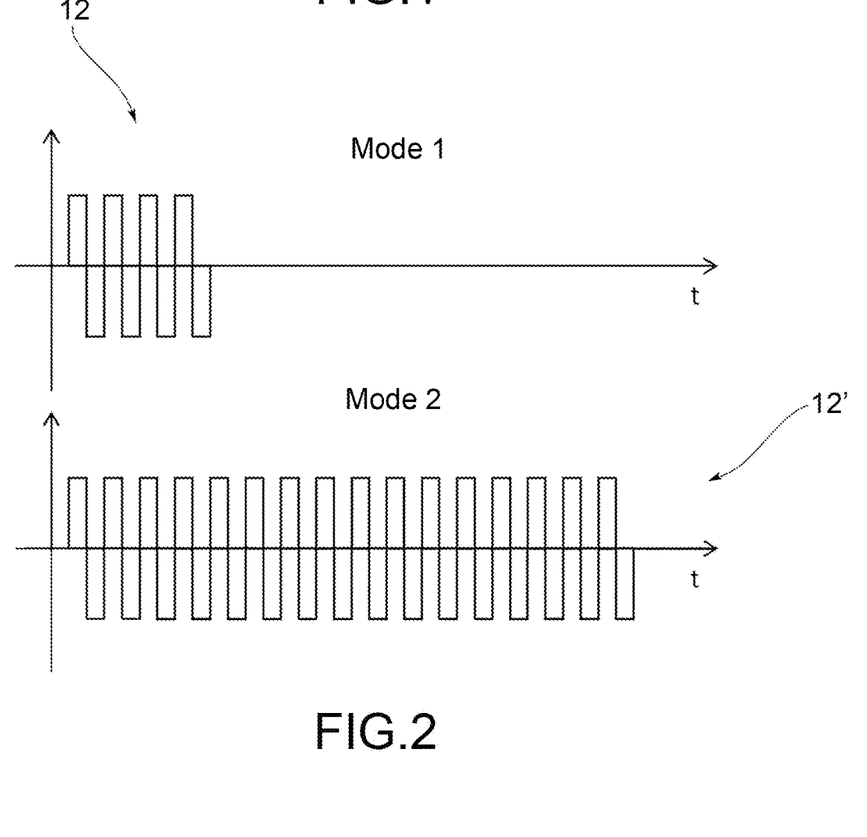
FIG. 2 shows two examples of pulse packets.

For example, FIG. 2 shows two pulse packets 12, 12': at the top, a pulse packet 12 which groups 4 bipolar pulses 10; at the bottom, a pulse packet 12' which groups 16 bipolar pulses 10.

Therefore, depending on the type of treatment to be carried out on the muscle group and/or depending on the type of muscle group, the following are defined:
  the duration of each sub-interval;
  the number of pulses in each pulse packet;
  the frequency Fpacc of the pulse packets, i.e. the time that must elapse between one pulse packet and the next;
  the amplitude and duration of each pulse.

The subdivision of the stimulation period ΔTseq into a plurality of sub-intervals SI of duration ΔTn, equal to each other and equal for all channels, allows all the channels to be synchronized.

Furthermore, as explained above, each stimulation period P of duration ΔTseq of each channel has a half-period Toff lacking basic pulse sequences and the other semi-period Ton with at least one stimulation sub-interval.

It should be noted that the bipolar pulse shape, with the same amount of electric charge in each half-period, is used to avoid the galvanic destruction of cables and electrodes. Furthermore, in this way ions are not redistributed into human tissues. In the case of a monopolar shape, the accumulation of acids and alkalis could occur under the polarized electrodes.

Thus, the stimulation sequence within each stimulation period is given by one or by one repetition of several base pulse sequences, wherein each base sequence is given by one or by one repetition of several pulse packets.

In one embodiment, the number of pulse packets and the number of pulses of each pulse packet in each stimulation sub-interval are the same for all channels.

In one embodiment shown in FIG. 3 for 16 channels, the number and/or time distribution of the stimulation sub-intervals of the stimulation period of one channel is different from the number and/or temporal distribution of the stimulation sub-intervals of at least one other channel.

As anticipated above, the cyclic movement obtained is carried out with the involvement of a large number of muscles that work in a programmed sequence. The main muscle groups have been selected and the clinical electromyography of the modes of the cyclical workout thereof for all basic types of human movement has been identified.

With these movement diagrams, a software library of functional electrostimulation programs was created on 16 independent channels.

Each muscle group involved in the movement is stimulated at the appropriate moment during the cycle time, depending on its function, period and type of motion.

The duration of the electrostimulation for each muscle corresponds to the myographic muscle period of activity and depends on the type of movement and the rhythm at which it is carried out.

Since for each program the degree of participation of each muscle group could be different, in one embodiment the duration of electrostimulation in each channel is strictly individual. The amplitude of the electrical signal is chosen individually for each channel when it is set until the muscle contraction is received without pain.

In pathology, including cases of total lack of muscular activity, specific programs of functional electrostimulation are used, suited to the specifics of the case. The basic model of reference, however, always remains the physiological one.

This methodological solution allows one to activate and construct dynamics to bring a pathological system back into the correct physiological direction.

Preferably, if a stimulation period has more than one stimulation sub-interval, the stimulation intervals are consecutive.

In one embodiment, the amplitude of the pulses of one channel is different from the amplitude of the pulses of at least one other channel.

In effect, the various parts of the body have different levels of sensitivity and different quantities of well-distributed, sensitive nerve endings (sensors).

Each sensor has strictly its own specific purpose: to inform the nervous center of all modifications to the processes. The majority of the sensory system is located in the sensitive neurons of the spinal cord ganglia that transmit information on the spinal level of the segment, where it is passed on to the appropriate centers, including the movement system. The results of integrated optimization and correction of this spinal level via the afferent pathways of the spinal cord are transmitted to the motor centers and the brain.

To ensure adequate neuromuscular functions, it must be taken into account that the amplitude of the signal varies with respect to the stimulated muscle sensitivity. In particular, on the musculature of the upper half of the body, the amplitude of the signal for activation is smaller than that necessary for the lower limbs.

For this reason, when configuring the various stimulation intensity modes, a signal amplitude is provided in each channel to ensure muscular contraction without pain for the patient.

When the pathology compromises the sensitivity of the neuromuscular system, such sensitivity may vary greatly between the left and the right half of the body (for example, in cases of hemiparesis).

In one embodiment, the amplitude of the first pulse or last pulse of a stimulation sequence of a channel is significantly greater than the amplitude of the remaining pulses. In this way, the muscle stimulated by this channel is prepared for a subsequent stimulation.

In one embodiment, sensory stimulation is associated with the electrical stimulation of the muscles, for example, in the form of a light and/or acoustic signal.

As stated above, the electrical stimulation takes place according to the preset program that accompanies the known cyclic motion performed in the specified rhythm. Any movement always begins with the contraction of certain muscle groups; the group that must start moving first is stimulated by a channel called the "leader" channel.

In each functional electrical stimulation program, stored in the memory of the electrostimulation apparatus, a leader channel is therefore allocated, which first sends an electrostimulus to the main group of muscles. With the contraction of this muscle, the movement of the group begins.

In one embodiment, the leader channel is connected to a sound and/or visual signal that operates simultaneously with the beginning of the cycle of the muscle group.

The patient starts moving on the program simultaneously with the acoustic and/or visual signal. In effect, the brain of the subject in exercise interfaces with the acoustic and/or visual signal of the leader channel to perform the exercise of the main muscle group according to the program, thus guaranteeing the synchronization of each recurring cycle.

Such arrangement allows the coordinated execution of the motor action according to the electrostimulation program, together with the activation of the movement control centers of the cerebral cortex, providing an activation of the necessary biochemical processes of neuromediation and centralized optimization of the movement control.

This is expressed in an increase in the excitation speed along the nerve fibers, in the organization of the interneuron system at the segmental level, in the vegetative maintenance of all these connections due to the summation and automation of the effects with the repetition of the motor action according to the program that involves the entire central nervous system.

In one embodiment, the leader channel, to which the emission of an acoustic and/or visual signal is associated, is the electrostimulation channel of the muscle group considered more important in the execution of the complex movement or more in need of stimulation and does not necessarily coincide with the channel that initiates each cycle of electrostimulation.

Therefore, in a preferred embodiment, for each program concerning a type of movement, a leader channel is identified, which represents the stimulation of the muscle group that is first activated (or, as mentioned above, of the most important muscle group) during the movement cycle. Following the activation of the leader channel, to complete the entire movement cycle, the remaining muscular channels/groups recruited to perform the motor act are activated. The next cycle starts again with the same channel activation sequence.

To each of the electrostimulation channels is assigned a certain and predetermined muscle group. For example, therefore, if a movement program A begins with activation of the right femoral biceps, such channel number 1 linked to such muscle group becomes the leader channel. As the programs/cycles of movement vary, the number of the leader channel will vary accordingly. This arrangement of combining the various muscle groups of each program with the respective electrostimulation channels allows one, among other things, to organize and simplify the mathematical algorithms of the management software of the electrostimulation apparatus. This is particularly important for the automatic synchronization of the electrical stimulation of the muscle groups recruited in the workout cycle when the movement rhythm is changed.

In accordance with a preferred embodiment, to guarantee the synchronization of the electrical stimulation with the actual muscular activity during exercise, a sensor-based monitoring system is provided that detects the effective duration of the movement cycle carried out by the patient or athlete.

For example, sensors that provide an "ON-OFF" signal that indicates a change in position of the limb or part of a limb are used. Such sensors are then positioned at points suitable for reading the position change, for example under the heel, on the elbow, on the knee.

For example, in the case of a sensor placed under the heel, the cycle time duration begins to be recorded when the same heel touches the ground for the first time until the next time it touches, indicating the end of the cycle.

In some embodiments, a double measurement is carried out which provides the average value of the cycle time.

The ulnar sensor, positioned on the elbow, or a sensor positioned on a knee, measuring a variation of the bending angle, is repeatedly changed.

In case of mismatch between the pre-determined cycle time of the electrostimulation program, set manually, and the actual cycle time provided by the measurements made by one or more sensors, the electrostimulation method provides an adjustment of the cycle time on all channels in order to adapt it to the measured cycle time.

For example, as a function of the measured cycle time, the duration of each sub-interval Si, as defined above, is recalculated and reset.

Figure 4:
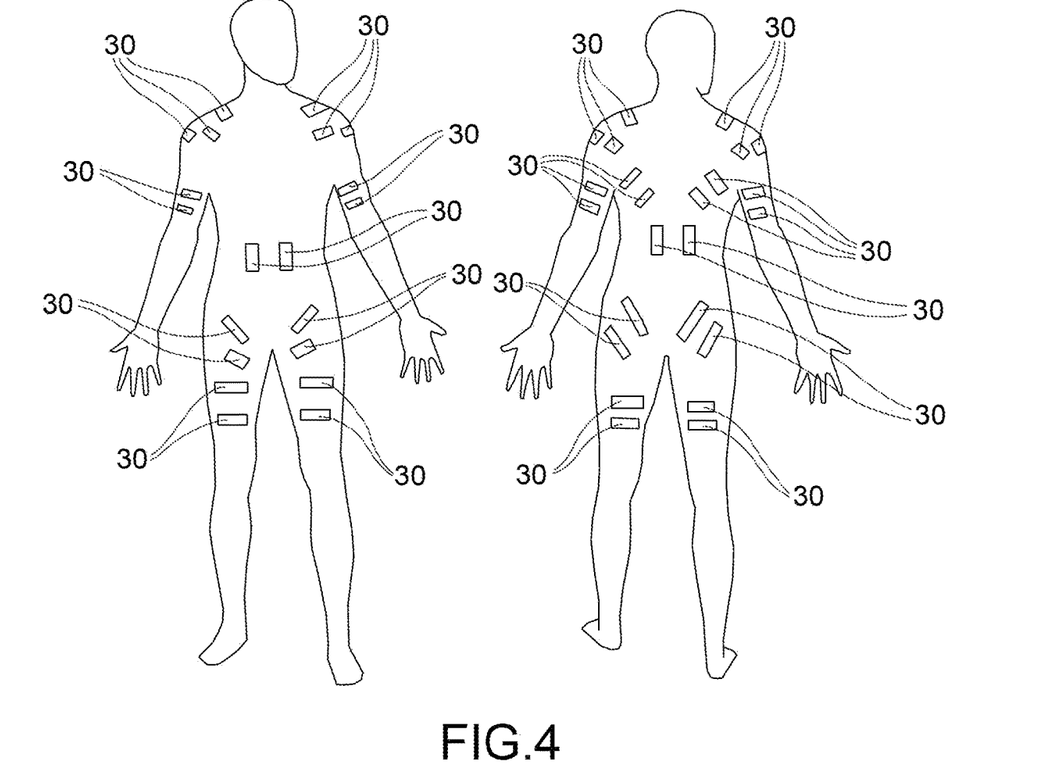
FIG. 4 shows the application of sixteen pairs of electrodes on the same number of muscle groups in the human body.
Figure 5:
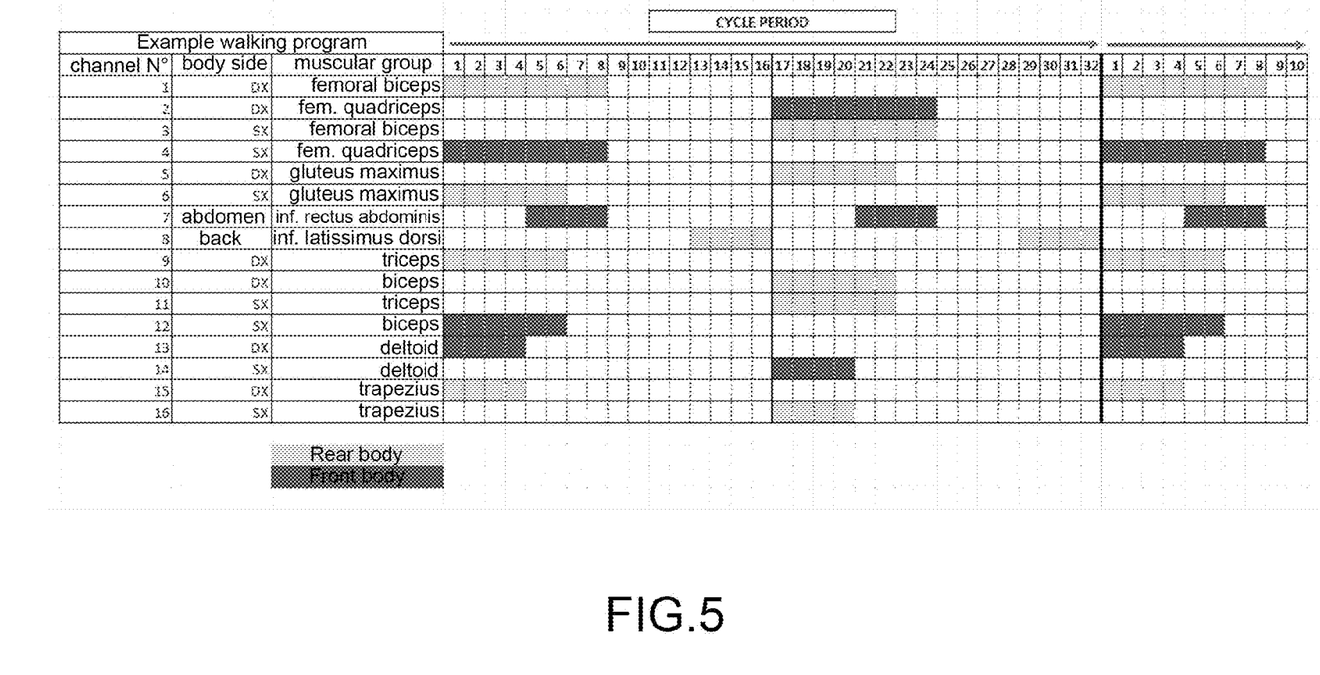
FIGS. 5, 5a and 5b show tables which represent, for each of the sixteen electrostimulation channels, the stimulation sequence of a workout program related to walking, running and squat exercise, respectively.
Figure 5A:
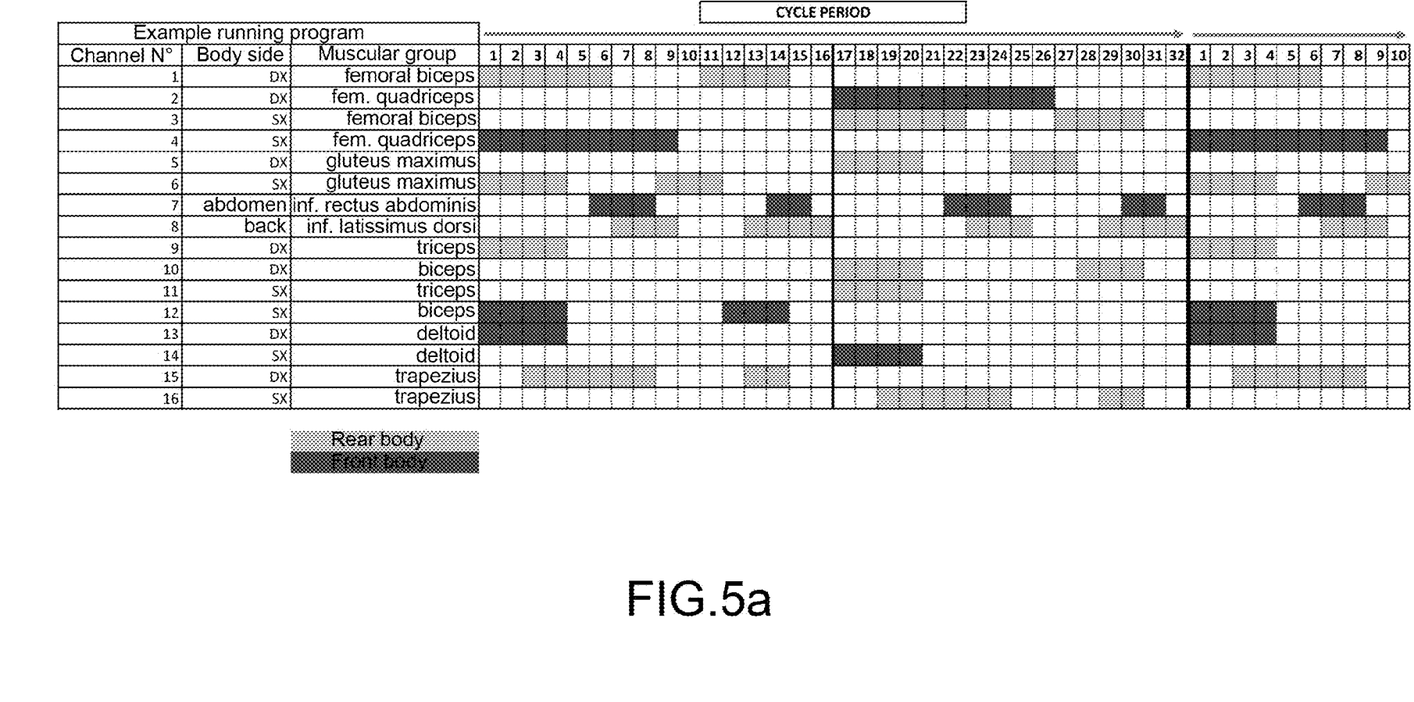
Figure 5B:
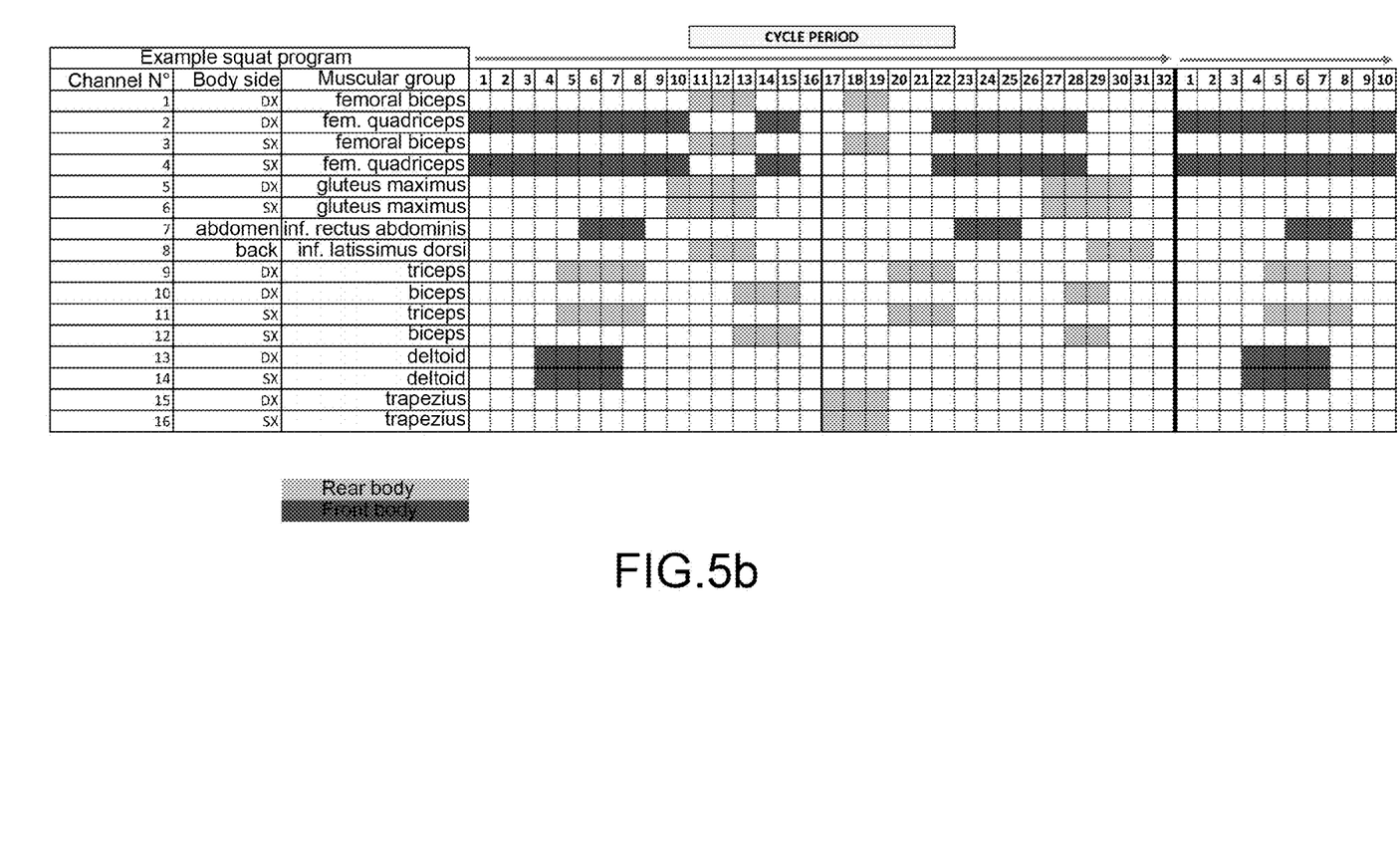
Figure 6:
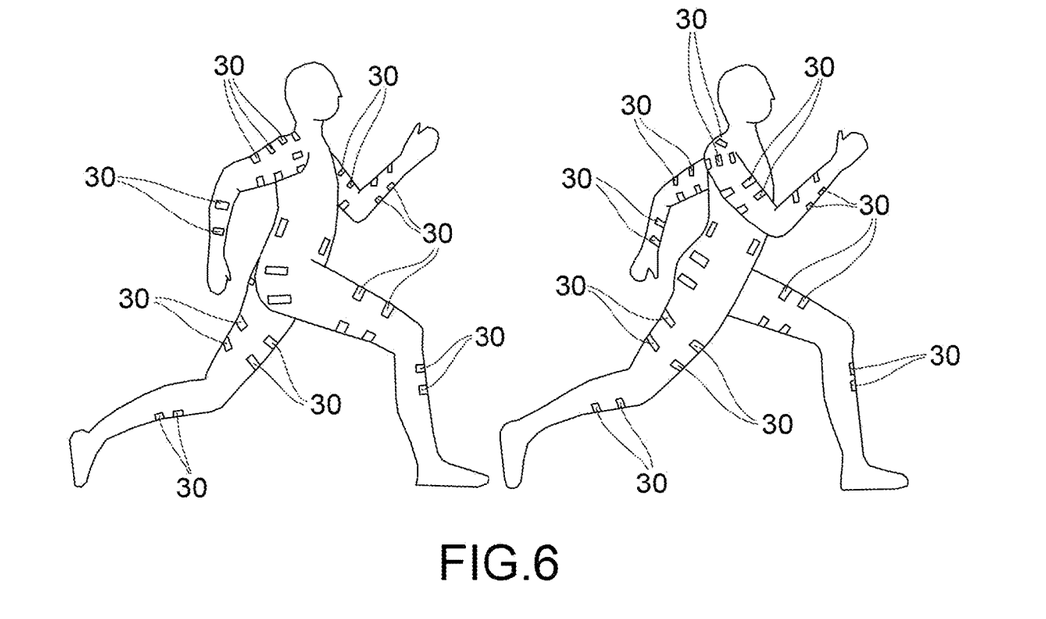
FIG. 6 shows the pairs of electrodes applied to the muscle groups involved in the "walking" workout program, in the two phases of the motor action.

With reference to FIGS. 4-6, examples of the electrostimulation program will now be described.

FIG. 4 shows the positioning of 16 channels, each comprising a pair of electrodes 30, on the patient's body. As explained above, each channel that stimulates a muscle group, for example a flexor muscle group, corresponds to a symmetric channel that stimulates a functional antagonist muscle group, for example an extensor muscle group, which causes the contraction of the muscle in phase opposition with respect to the cyclical movement.

The workout program of the functional electrical stimulation illustrated in FIG. 5 is related to the walking movement.

The complete period of a functional electrical stimulation cycle is presented on the graphs of FIGS. 5, 5a and 5b, in the case of walking, running and squat exercise, respectively. On the left side of the diagram are indicated the 16 muscle groups stimulated by 16 respective channels. The two central columns show the operating diagram for each channel during a complete movement cycle. The last column on the right represents the first ten sub-intervals of a new cycle.

The complete period of a cycle is divided into 32 phases. Each of the phases of the cycle is 1/32 of the period.

The period may vary from 0.2 to 10 seconds. Each repetition cycle always begins with the same group of muscles. The entire movement cycle is divided into two parts.

For example, in the case of walking (FIG. 5) the leader channel, to which an acoustic or visual signal is associated, is the one that determines the beginning of the movement of the right leg. Sequentially, the second half of the cycle determined by the movement of the left leg begins until it reaches the phase 32.

More specifically, each movement cycle is, for simplicity, divided into a certain number of sub-intervals (for example, 32). For each program it is possible to pair with one of the 16 electrical channels (in the fundamental group for that type of program) the above-mentioned acoustic signal.

The arms follow the dynamics of walking, with an appropriate reciprocal movement.

With reference to FIGS. 7-10, a practical example of an apparatus 50 capable of carrying out the electrostimulation method described above will now be described.

Figure 7:
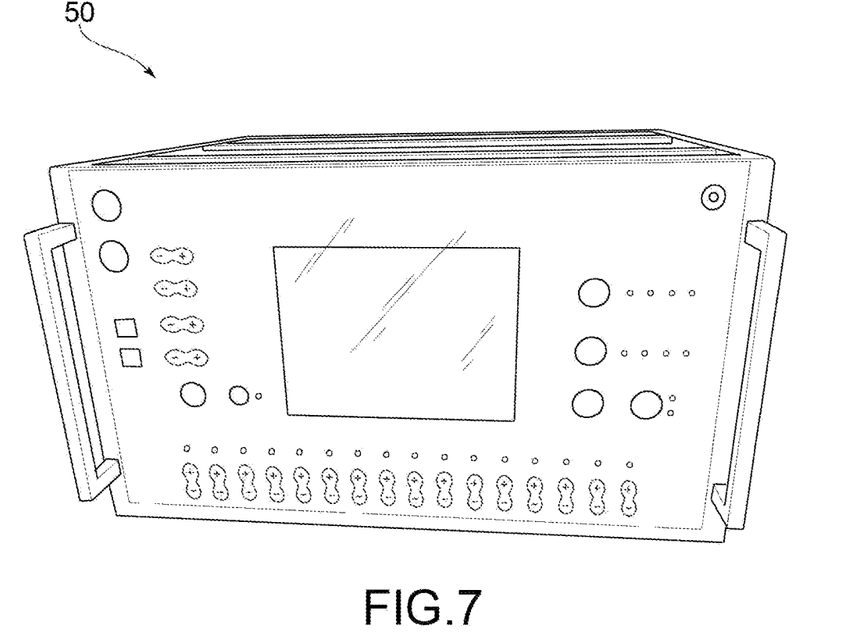
FIG. 7 is a front view of an electrostimulation apparatus according to the invention.
Figure 8:
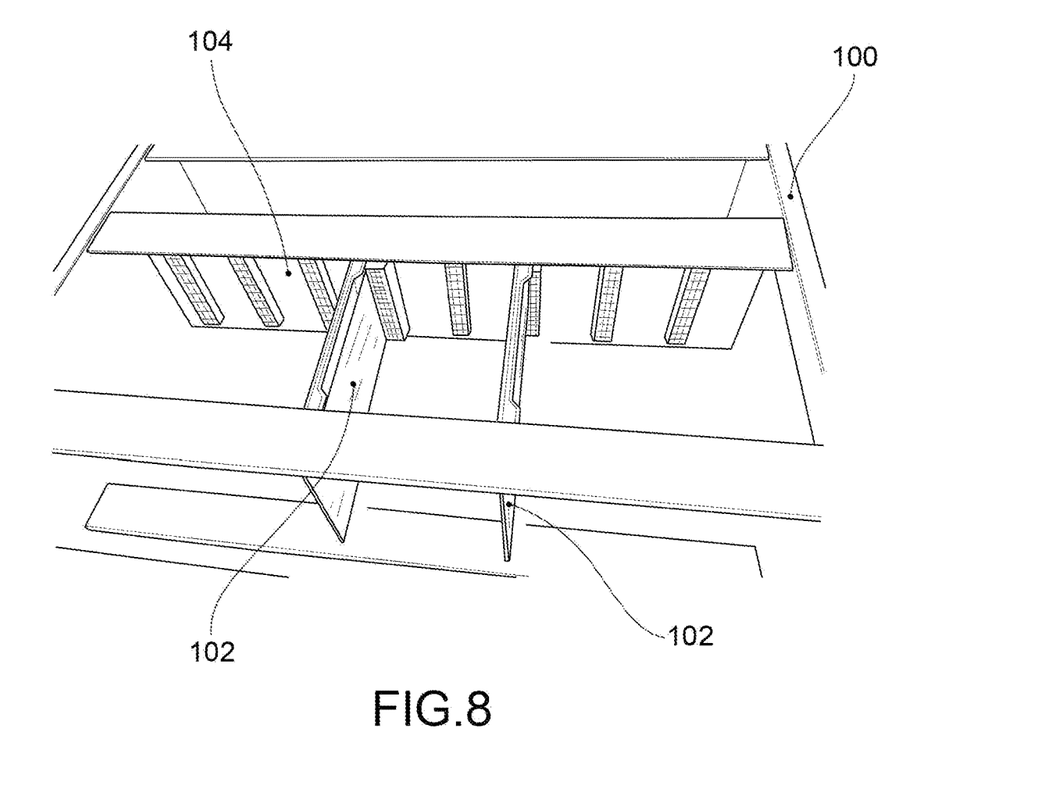
FIG. 8 shows the power boards connected to the backplane.
Figure 9:
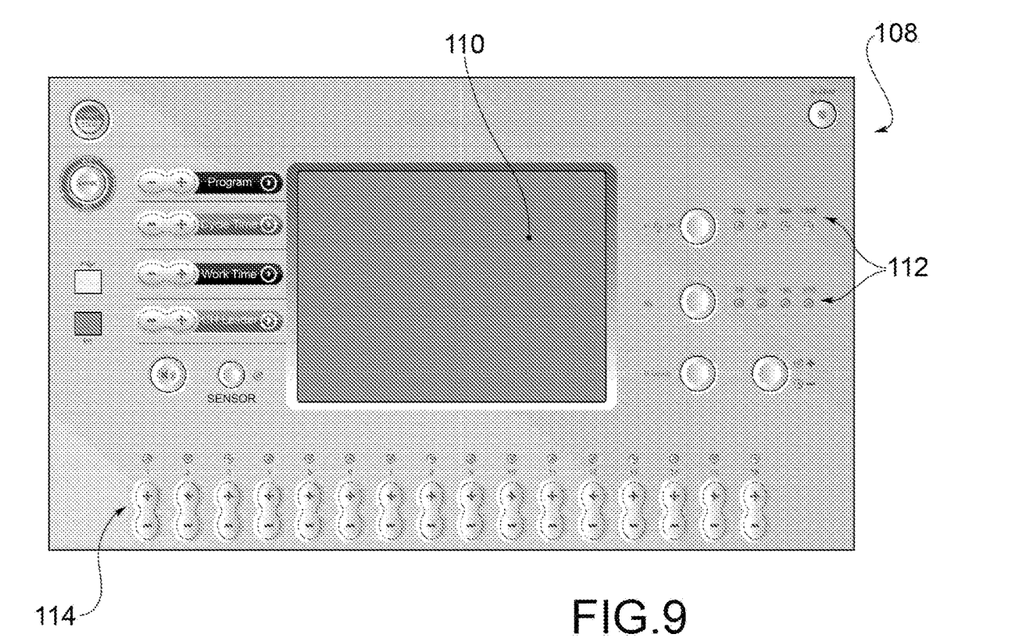
FIG. 9 shows the user interface.

The apparatus comprises a frame 100 which supports eight two-channel power boards 102, a backplane 104 for connecting the power boards 102, an electronic processing unit 106 and a user interface 108.

For example, the apparatus 50 is powered by means of a universal power supply (85-264 Vac input) approved for the electro-medical sector (IT & Medical Safety Approvals (Class I & II)).

In one embodiment, the current of each channel is controlled and is capable of delivering a maximum current of 150 mA with a nominal load of 1 kOhm (so for each channel the maximum voltage is 150V).

In one embodiment, the user interface 108, shown in FIG. 9, comprises an 8-color TFT display 110, a plurality of signaling LEDs 112 and a plurality of buttons 114, the functions of which will be described hereinafter.

The management of the user interface is entirely the responsibility of the electronic processing unit 106.

The user interface 108 allows the user to perform a first programming phase and a second execution phase. During the first programming phase, it is possible to select which programs will be part of the sequence to be executed (second phase) and, for each program, the related parameters. During the second phase (execution phase) the programs selected during the first phase are executed one by one.

The buttons perform the following functions:

START/STOP button: Allows the current program sequence to be started or stopped;

ENTER button: this button performs various functions:
pressing for less than two seconds during the programming phase forces the current program in the sequence to be saved (selecting it therefore for execution);
pressing it for more than two seconds during the programming phase allows the initial direction of the pulses (positive or negative), i.e. afferent or efferent, to be selected for all channels,
pressing it while a program is running forces the immediate passage to the next program (or ends the sequence if the current program was the last).

PROGRAM +/− buttons: allow a program to be selected from those in the library. These buttons are active only during the programming phase;

CYCLE TIME +/− buttons: allow the cycle time to be changed between 200 ms and 10 s with a 200 ms time step. These buttons are active only during the programming phase;

WORK TIME +/− buttons: allow the workout time (duration of the program) to be changed. The time step is 1 minute. These buttons are active only during the programming phase;

CH.LEADER +/− buttons: allow the leader channel to be selected. These buttons are active only during the programming phase;

SOUND button: allows the sound relative to the leader channel (if selected) to be enabled/disabled;

SENSOR button: allows an external sensor to be used;

INTENSITY +/− buttons: allow the intensity (amplitude) of the pulses to be changed. These buttons are active only during the execution phase;

PULSE TIME button: allows the elementary pulse duration to be selected. This button is active only during the programming phase;

FREQUENCY button: allows the repetition frequency of the pulse packets to be selected. This button is active only during the programming phase;

MONO button: allows, for the leader channel only, monopolar or bipolar pulses to be used. This button is active only during the programming phase;

+/− button: in the case of monopolar pulses for the leader channel, it allows one to specify whether the pulses are positive or negative. This button is active only during the programming phase;

As for the use of at least one external sensor 123, as mentioned above, all the cyclical movements are repeated with a predetermined frequency. The cycle time is measured in seconds. Naturally, the shorter the cycle, the faster the movement is and vice versa.

To measure the cycle time of the movement, it may be convenient to use a sensor associated with a movement. For example, a heel sensor may be used located in the footbed of the patient's footwear. Such sensor detects the execution of a step.

In another embodiment, a goniometric sensor may be used, which measures changes in the peak angle in the joint, or a position sensor.

In the case of a change in rhythm (slowing down from fatigue or acceleration), that is, when a patient's movement rhythm changes with respect to the predetermined electrostimulation frequency, an automatic correction of the cycle time of the stimulation based on the actual data provided by the sensor or sensors comes into play.

Figure 10:
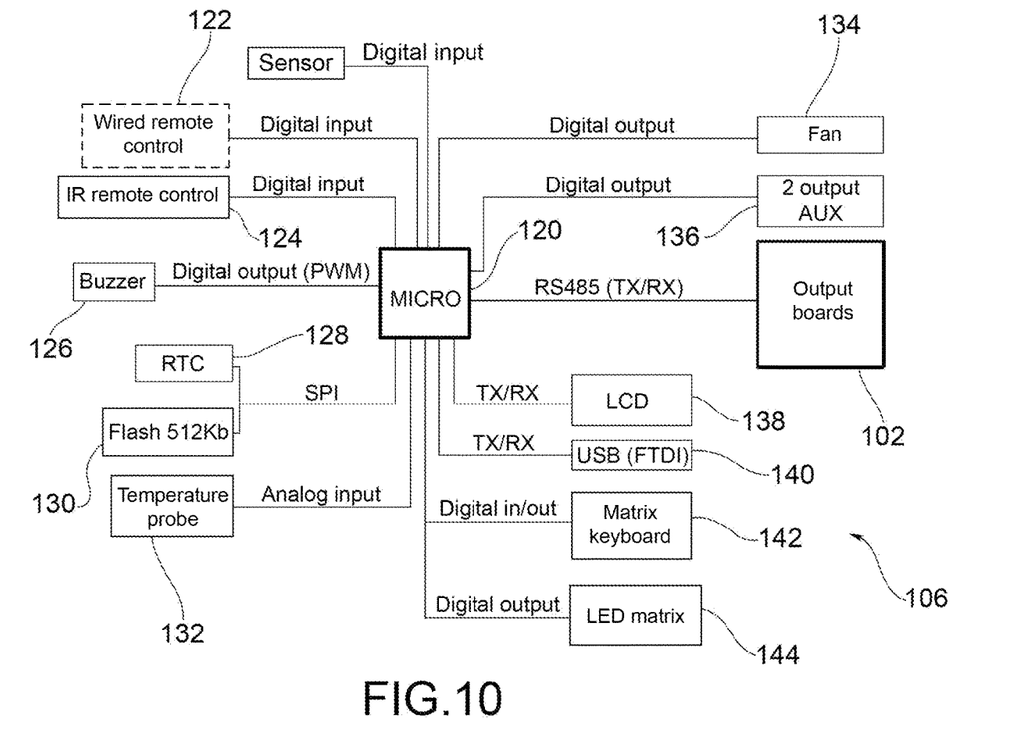
FIG. 10 is a block diagram of the microprocessor control unit.

Each external sensor supplies to the electronic processing unit 106, through an appropriate electronic conditioning system, an electrical signal, for example a digital ON/OFF, used by the electronic processing unit to recalculate and reset the cycle time of the electrostimulation program.

FIG. 10 shows a block diagram of the electronic processing unit 106. This electronic processing unit is implemented with a microcontroller 120 which manages:
- an Input for the external sensor 122;
- an infrared remote-control Input 124 for START/STOP of the remote programs (digital input);
- a buzzer 126 for managing the sound relative to the leader channel (digital output PWM);
- a Real-time clock 128 (via SPI interface);
- an external Flash memory 130 for storing programs, etc. (via SPI interface);
- a temperature probe 132 (analog input);
- a cooling fan 134 (digital output);
- two digital outputs 136 (to the power boards);
- an LCD display 138 (via UART);
- a USB interface 140 for connection to a personal computer (via UART);
- digital inputs and outputs for buttons 142 (key matrix);
- digital outputs 144 for LEDs.

Each two-channel power board 102 is capable of handling two output channels. For each channel, pulse sequences at a variable frequency and/or intensity are generated, for example as described further on.

Since the proposed electrostimulation method is based on the recruitment of reciprocal muscle groups, each power board controls two channels that work sequentially.

It should be emphasized that this design choice is also useful to prevent a possible operator error, in particular, to avoid simultaneous action and the stimulation of the antagonist muscles that may cause a violation in the neural circuit operation of the interneuronic unit at the segmental level (Renshaw cell).

In one embodiment, the single pulse is bipolar, symmetrical, and squared as shown in FIG. 1.

In one embodiment, the maximum pulse width Aimp is 150 V (hence 300 V peak-to-peak) and its duration DTimp may be selected from the following values: 100 µs-200 µs (default)-500 µs-1000 µs.

In one operating mode (mode 1), the pulses are grouped into packets of four consecutive pulses; in another operating mode (mode 2) the pulses are grouped into packets of 16 consecutive pulses.

In the hypothesis that each pulse lasts 200 µs (default), in mode 1 each package therefore lasts about 0.8 ms while in mode 2 each package lasts about 3.2 ms.

The packets are repeated with a selectable frequency Fpacc between the following values: 50 Hz-100 Hz-150 Hz-200 Hz (between one pulse packet and the next one there is a time DTpacc selectable between the following values: 5 ms-6.67 ms-10 ms-20 ms).

Naturally, packets may consist of a different number of pulses, for example 5 or 10 pulses.

The sequences of the pulse packets are repeated identically at intervals DTseq, with cycle time DTseq variable from 200 ms to 10 s at 200 ms steps. Each interval DTseq is in turn divided into N=20 sub-intervals DTn of equal duration, as illustrated for example in FIG. 3.

Moreover, each interval DTseq is divided into two intervals (TON and TOFF) of equal duration; during the TON interval there are pulse packets, while during the TOFF interval there are no packets. For example, in FIG. 3 for channel n. 1 the TON time includes the sub-intervals 1-10, while the TOFF time includes the sub-intervals 1-20. On the other hand, for channel n. 2 the TON time includes the sub-intervals 11 20 while the TOFF time includes the sub-intervals 1-10.

Within each sub-interval DTn one may then have (depending on the programmed characteristics of the sequence):
- no pulse packet, or
- a train of pulse packets (represented in FIG. 3 as a 'full' square) with the characteristics described above.

In one embodiment, the characteristics of the packets (number of pulses per packet, time interval between one packet and the next) and the interval DTseq are the same for all channels, while the amplitude may vary from channel to channel.

For example, DTseq=1 s⇒DTn=1000 ms/20=50 ms. Assuming that each pulse lasts 200 µs (default), that the mode 2 is used (n. 16 pulses⇒3.2 ms) and that DTpacc=10 ms, each sub-interval DTn wherein pulses are present will contain four packets.

In the event that a packet is straddling two consecutive sub-intervals DTk and DTk+1 where the sub-interval DTk+1 does not contain packets, the packet itself is truncated at the end of DTk. If on the other hand the sub-interval DTk+1 also contains packets, the packet continues in this second sub-interval.

Each program is therefore fully defined by the following parameters:
- for each channel in which sub-intervals are present the pulse packets;
- cycle time;
- workout time;
- duration of the elementary pulse;
- number of pulses per packet;
- leader channel (if present) and characteristics of the pulses of such channel (monopolar or bipolar);
- direction of the pulses (afferent or efferent);
- frequency of pulse packets.

It should be noted that when a program is running, both the cycle time and the pulse amplitude may vary.

Operationally, the electrostimulation procedure is performed as follows:
1. a program selected using the PROGRAM +/− buttons;
2. parameters chosen for the selected program;
3. the ENTER button pressed to confirm; the selected program is then added (queued) to the sequence of programs to be executed;
4. steps 1 to 3 repeated for each program that one wishes to add to the sequence;
5. the sequence of the programs selected started by the START button or by remote control;
6. if one wishes to end the whole sequence prematurely, the STOP button is pressed; if instead during the execution of the sequence one wishes to interrupt the execution of the current program to go to the next program, the ENTER button is pressed.

In summary, the proposed electrostimulation method and apparatus are based on synchronous electromyostimulation of the main muscle groups of the body during cyclical movements, i.e. repeated, respecting the physiological models of the human movement being executed.

In other words, the moment of the activation of the electrical stimulus sent to a muscle group at the specified frequency coincides with the voluntary physical activity that the patient performs at that moment.

Consequently, the muscle fibers are activated, supporting and strengthening the function of the sensory system at the spinal level, helping to monitor the implementation of each movement cycle and to activate of the necessary motor neurons.

In cases where electrostimulation of the muscles is not synchronized with the movement, as occurs in current electrostimulation apparatuses, it is possible, on the contrary, that a negative effect occurs, because the sensory system at the spinal level may forcefully impose a mode of operation that does not correspond to its functionality.

It is especially important to take this into account during rehabilitation sessions of the various forms of pathology and trauma with loss of sensitivity.

Consequently, one obtains a workout of the segmental spinal system responsible for coordinated and synchronized muscular contraction that is more precise and rapid in the correction of movements and in the rational control of traffic up to the segmental level.

The proposed electrostimulation method and apparatus are able to train the neuro-muscular system in such a way as to obtain a level and a response speed that cannot be achieved with the stimulation methods of the state of the art. In particular, an increase in speed, endurance, and athletic performance is obtained, with reduced manifestation of muscular injuries, which become more predictable and controllable.

The proposed method of electrostimulation, based on the physiological models of the human neuromuscular system, allows the process of muscle contraction to be optimized, and more precisely to:

increase the explosive strength of muscle contraction due to the electrical activation of high-threshold motor units. If, during the maximum muscle contraction of the human muscle, no more than 70% of the muscle fibers of the muscle are activated, through the combination with electrostimulation according to the invention, the number of simultaneously activated muscle fibers may approach 100%. Such activation significantly improves muscle power;

increase the synchronization of the sensory system at the spinal level, which manages the control of muscle contraction. With the action of a further rhythmic electrical activation (as is the case of a heart pacemaker) synchronized with the execution of a function, the sensory system of the muscles is regulated to the rhythm of the movement, with the development of a resonance phenomenon through which simultaneous information is sent to the overlying nerve centers through the available neural pathways. Since the electrical activation mode takes into account the physiological characteristics at the cellular level, such type of cyclical functioning of the neuromuscular connection leads to the optimization of the biochemical processes of muscle contraction and transmission of the excitation along the nerves, and also to an increase in size of the motor neurons. Consequently, there is an increase in the number of synapses with consequent increase in the reliability of synaptic transmission due to the imprinting of operating modes optimized at the level of cellular memory;

increasing the speed of information that reaches the cortical centers in the ascending direction without blocking spinal protection, since the information on the workout performed is compatible with theories and physiological models.

To train the athletes' stamina qualities, it is possible to perform electrical stimulation for any program with a speed approaching the level of the physiological maximum. This means that in 1 second it is possible to perform 5 complete cycles of movement for one limb (100 ms for the cutoff phase and 100 ms during the relaxation phase). Naturally, the second branch of the reciprocal regime will begin the same movement during the relaxation phase of the first one.

Through the proposed method of electrostimulation, it is also possible to contain and improve the severe and debilitating condition of "back pain", by ensuring the correct operation of the muscular corset essential for good posture.

Moreover, it is possible to follow the various phases of sports training through continuous monitoring of the vital functions of the patient, which is very important for defining, during the stimulation, the type of training to follow and the intensity to be obtained.

To the embodiments of the electrostimulation method and apparatus according to the invention, one skilled in the art may, to satisfy contingent needs, make modifications, adaptations and replacements of some elements with others that are functionally equivalent, without departing from the scope of the following claims. Each of the features described as belonging to a possible embodiment may be implemented independently from the other described embodiments.

The invention claimed is:

1. An electrostimulation method of at least one muscle group responsible for performing a complex cyclic movement, the method comprising the steps of:

creating an electrostimulation program based on an electromyographic recording of the complex cyclic movement, wherein the electrostimulation program is adapted to provide synchronized electrostimulation of the muscles of the at least one muscle group to allow reproduction of the complex cyclic movement;

associating to each of the muscles of the at least one muscle group an electrostimulation channel provided with at least one respective electrode, each electrostimulation channel being adapted to transmit to a respective muscle bipolar electrical pulses in sequence;

determining, for all the electrostimulation channels, a same cycle time defining a repeatable period of stimulation, wherein within said stimulation period each channel performs an associated stimulation sequence according to the electrostimulation program;

sub-dividing each stimulation period into two half-periods of equal duration;

sub-dividing each half-period into a plurality of sub-intervals of a same duration, wherein at least one of said sub-intervals is a stimulation sub-interval in which a basic sequence of pulses comprising one or more pulse packets is performed, each pulse packet being given by a predetermined sequence of individual bipolar electric pulses, and wherein each stimulation period of each channel has a half-period free of basic pulse sequences and has an other half-period with at least one stimulation sub-interval, and at least two stimulation periods of respective channels have different half-periods lacking basic pulse sequences.

2. The method according to claim 1, wherein the number of pulse packets and the number of pulses of each pulse packet in each stimulation sub-interval are the same for all channels.

3. The method according to claim 1, wherein the number and/or the temporal distribution of the stimulation sub-intervals of the stimulation period of one channel are different from the number and/or from the temporal distribution of the stimulation sub-intervals of at least one other channel.

4. The method according to claim 1, wherein, if a stimulation period has more than one stimulation sub-interval, the stimulation intervals are consecutive.

5. The method according to claim 1, wherein the amplitude of the pulses of one channel is different from the amplitude of the pulses of at least one other channel.

6. The method according to claim 1, wherein an amplitude of a first pulse or last pulse of a stimulation sequence of a channel is greater than an amplitude of remaining pulses.

7. The method according to claim 1, further comprising the step of associating with activation of a predetermined electrostimulation channel emission of an acoustic and/or visual signal perceptible to a person subjected to the electrostimulation method.

8. The method according to claim 7, wherein said predetermined electrostimulation channel is the electrostimulation channel which is activated to initiate each stimulation period.

9. The method according to claim 1, further comprising the steps of:
  detecting, through a sensor-based monitoring system applied to at least one limb or limb portion, an effective duration of a cycle of the complex cyclic movement performed by a patient or athlete;
  comparing the predetermined cycle time of the electrostimulation program with an actual cycle time provided by the monitoring system and, in the event of a mismatch,
  adjusting the cycle time of the electrostimulation program to adapt the cycle time to a measured cycle time.

10. The method according to claim 9, wherein regulation of the cycle time of the electrostimulation program is carried out by recalculating and resetting a duration of each sub-interval.

11. An electrostimulation apparatus to stimulate at least one muscle group responsible for performing a complex cyclic movement, comprising:
  a plurality of electrostimulation channels provided with at least one respective electrode; each electrostimulation channel being adapted to transmit to a respective muscle bipolar electrical pulses in sequence;
  at least one power board to generate sequences of electric pulses;
  storage means in which at least one electrostimulation program is stored;
  an electronic control unit to control the power boards according to an electrostimulation program stored in the storage means;
  wherein:
    said electrostimulation program is based on an electromyographic recording of the complex cyclic movement and is adapted to provide synchronized electrostimulation of the muscles of the at least one muscle group so as to allow reproducing the complex cyclic movement;
    said electrostimulation program is given by repetition, on each electrostimulation channel, of electrostimulation periods or intervals having a same cycle time, wherein an associated stimulation sequence is defined within each stimulation period for each channel;
    each stimulation period is divided into two half-periods of equal duration;
    each half-period is divided into a plurality of sub-intervals of equal duration;
    at least one of the sub-intervals is a stimulation sub-interval wherein a base sequence of pulses comprising one or more of pulse packets is executed;
    each pulse packet is given by a predetermined sequence of individual bipolar electric pulses;
    wherein each stimulation period of each channel has a half-period free of basic pulse sequences and has an other half-period with at least one stimulation sub-interval, and at least two of the stimulation periods of respective channels have different half-periods free of basic pulse sequences.

12. Apparatus according to claim 11, wherein each power board is adapted to generate symmetrical and squared sequences of bipolar electric pulses, each bipolar pulse consisting of a square wave having a pulse period divided into two half-periods of equal duration, one of positive amplitude and the other of negative amplitude.

13. Apparatus according to claim 11, wherein the number of pulse packets and the number of pulses of each pulse packet in each stimulation sub-intervals are the same for all the channels.

14. Apparatus according to claim 11, wherein the number and/or the temporal distribution of the stimulation sub-intervals of the stimulation period of a channel is different from the number and/or the temporal distribution of the stimulation sub-intervals of at least one other channel.

15. Apparatus according to claim 11, comprising means for generating an acoustic and/or visual signal operatively connectable, selectively, to one of the electrostimulation channels so that, upon activation of said electrostimulation channel, an audible and/or visual signal perceptible to the subject undergoing the electrostimulation treatment is generated by the means for generating an acoustic and/or visual signal.

16. Apparatus according to claim 11, comprising at least one sensor applicable to at least one limb or limb portion and to generate a signal indicative of an actual duration of the complex cyclic movement, the electronic control unit being adapted to receive the signal generated by at least one sensor and being configured to:
  compare a predetermined cycle time of the electrostimulation program with an actual duration of the complex cyclic movement and, in case of mismatch,
  automatically adjust the cycle time of the electrostimulation program to adapt the cycle time to the actual duration of the complex motion measured.

* * * * *